United States Patent
Zhen et al.

(10) Patent No.: US 8,383,349 B2
(45) Date of Patent: Feb. 26, 2013

(54) BONE MORPHOGENETIC PROTEIN ANTAGONIST AND USES THEREOF

(75) Inventors: Hanson Zhen, Stanford, CA (US); Julie Sneddon, Palo Alto, CA (US); Patrick O. Brown, Stanford, CA (US); Anthony Oro, Standford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 909 days.

(21) Appl. No.: 12/075,944

(22) Filed: Mar. 13, 2008

(65) Prior Publication Data

US 2009/0041757 A1   Feb. 12, 2009

Related U.S. Application Data

(60) Provisional application No. 60/918,433, filed on Mar. 16, 2007.

(51) Int. Cl.
| C12Q 1/68 | (2006.01) |
| G01N 33/53 | (2006.01) |
| G01N 33/567 | (2006.01) |
| G01N 33/48 | (2006.01) |
| G01N 33/566 | (2006.01) |

(52) U.S. Cl. ...... 435/6.14; 435/6.1; 435/6.17; 435/6.19; 435/7.1; 435/7.21; 435/40.51; 435/40.52; 435/960; 436/501; 436/503; 436/63; 436/64

(58) Field of Classification Search ............... 435/6, 7.1, 435/6.1, 6.14, 6.17, 6.19, 7.21, 40.51, 40.52, 435/960; 436/501, 503, 63, 64
See application file for complete search history.

(56) References Cited

FOREIGN PATENT DOCUMENTS

| WO | 2006/019357 | 2/2006 |
| WO | 2006/048266 | 5/2006 |
| WO | 2006/094286 | 9/2006 |

OTHER PUBLICATIONS

Avsian-Kretchmer, O., et al. Molecular Endocrinology, 18(1): 1-12, 2004.*
Yanagita, M. et al., Cytokine & Growth Factor Reviews, 16: 309-317, 2005.*
Stabile, H., et al., Blood. 109: 1834-1840, 2007; epub Oct. 31, 2006.*
Lohela, M., Current Opinion in Genetics & Development, 20: 1-7, 2009.*
Hsu, David R.; et al., "The Xenopus Dorsalizing Factor Gremlin Identifies a Novel Family of Secreted Proteins that Antagonize BMP Activities", Molecular Cell, Apr. 1998, 1:673-683.
Khokha, Mustafa K; et al., "Gremlin is the BMP antagonist required for maintenance of Shh and Fgf signals during limb patterning", Nature Genetics, Jul. 2003, 34(3):303-307.
Namkoong, Hong; et al., "The bone morphogenetic protein antagonist gremlin I is overexpressed in human cancers and interacts with YWHAH protein", BMC Cancer, 2006, 6(74):1-13.
Sneddon, Julie B.; et al., "Bone morphogenetic protein antagonist gremlin 1 is widely expressed by cancer-associated stromal cells and can promote tumor cell proliferation", PNAS, Oct. 3, 2006, 103(40):14842-14847.
Topol, L.Z.; et al, "DRM/GREMLIN (CKTSF1B1) maps to human chromosome 15 and is highly expressed in adult and fetal brain", Cytogenet Cell Genet, 2000, 89:79-84.

* cited by examiner

*Primary Examiner* — Alana Harris Dent
*Assistant Examiner* — Anne Holleran
(74) *Attorney, Agent, or Firm* — Bozicevic, Field & Francis LLP; Pamela J Sherwood

(57) ABSTRACT

The present invention relates to the use of proteins that are differentially expressed in tumor associated stromal cells, as compared to normal stromal, as biomolecular targets for tumor treatment therapies. The present invention also provides compounds and pharmaceutically acceptable compositions for administration in the methods of the invention.

4 Claims, 9 Drawing Sheets
(9 of 9 Drawing Sheet(s) Filed in Color)

FIGURE 8
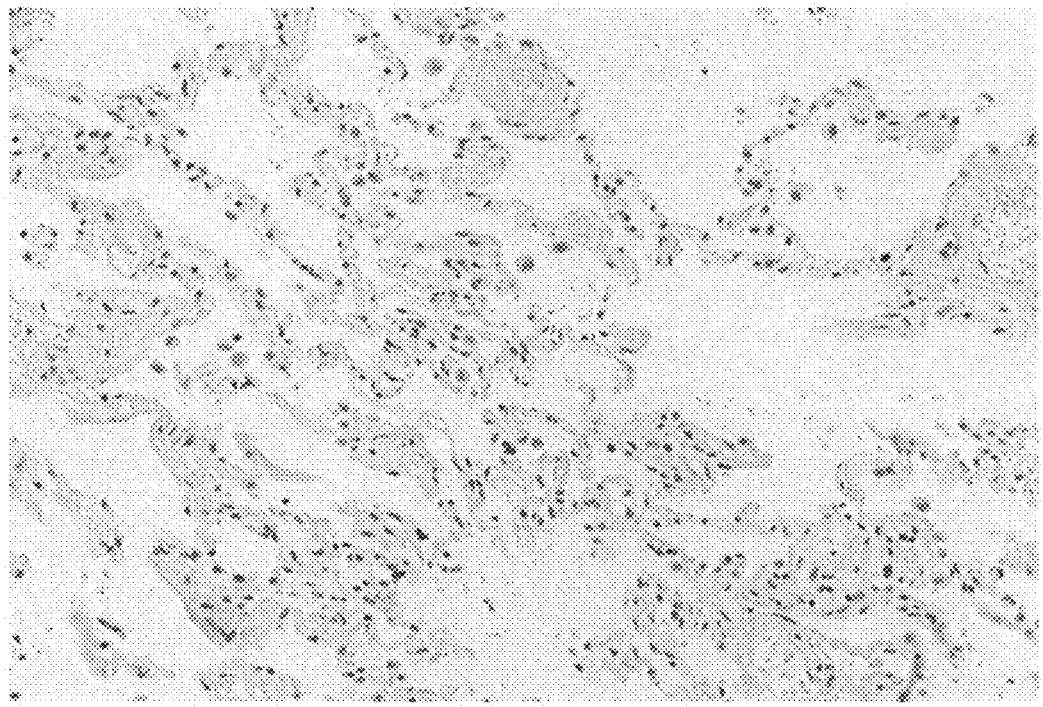
non-tumor
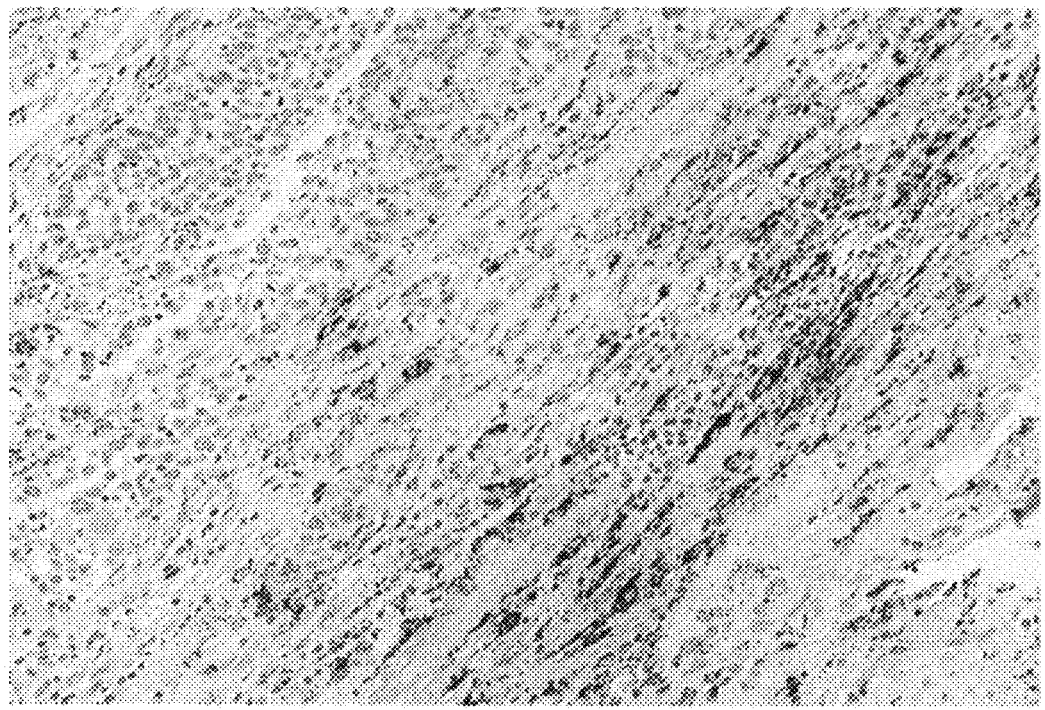
tumor

SEQUENCE LISTING

<160> NUMBER OF SEQ ID NOS: 6

<210> SEQ ID NO 1
<211> LENGTH: 628
<212> TYPE: DNA
<213> ORGANISM: homo sapien

<400> SEQUENCE: 1

```
gaggacccgc cgcactgaca gtatgagccg cacagcctac acggtgggag ccctgcttct      60
cctcttgggg accctgctgc cggctgctga agggaaaaag aaagggtccc aaggtgccat     120 cccccgcca gacaaggccc agcacaatga ctcagagcag actcagtcgc cccagcagcc     180
tggctccagg aaccgggggc ggggccaagg gcggggcact gccatgcccg gggaggaggt     240
gctggagtcc agccaagagg ccctgcatgt gacggagcgc aaatacctga agcgagactg     300
gtgcaaaacc cagccgctta agcagaccat ccacgaggaa ggctgcaaca gtcgcaccat     360
catcaaccgc ttctgttacg gccagtgcaa ctctttctac atccccaggc acatccggaa     420
ggaggaaggt tcctttcagt cctgctcctt ctgcaagccc aagaaattca ctaccatgat     480
ggtcacactc aactgccctg aactacagcc acctaccaag aagaagagag tcacacgtgt     540
gaagcagtgt cgttgcatat ccatcgattt ggattaagcc aaatccaggt gcacccagca     600
tgtcctagga atgcagcccc aggaagtc                                       628
```

<210> SEQ ID NO 2
<211> LENGTH: 184
<212> TYPE: PRT
<213> ORGANISM: homo sapien

<400> SEQUENCE: 2

Met Ser Arg Thr Ala Tyr Thr Val Gly Ala Leu Leu Leu Leu Leu Gly
1               5                   10                  15

Thr Leu Leu Pro Ala Ala Glu Gly Lys Lys Lys Gly Ser Gln Gly Ala

```
                20                  25                  30
Ile Pro Pro Asp Lys Ala Gln His Asn Asp Ser Glu Gln Thr Gln
         35                  40                  45

Ser Pro Gln Gln Pro Gly Ser Arg Asn Arg Gly Arg Gly Gln Arg
 50                  55                  60

Gly Thr Ala Met Pro Gly Glu Val Leu Glu Ser Ser Gln Glu Ala
 65                  70                  75                  80

Leu His Val Thr Glu Arg Lys Tyr Leu Lys Arg Asp Trp Cys Lys Thr
                 85                  90                  95

Gln Pro Leu Lys Gln Thr Ile His Glu Glu Gly Cys Asn Ser Arg Thr
        100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
        130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180
```

```
<210> SEQ ID NO 3
<211> LENGTH: 874
<212> TYPE: DNA
<213> ORGANISM: homo sapien

<400> SEQUENCE: 3
gaggcgcggc ctggcctcgc actcaaagcc gccgcagcgc gccccgggct cggccgaccc     60
ggcgggatc tagggtgggg cgacttcgcg ggaccgtggc gcatgtttcc tgggagttac    120
tgatcatctt ctttgaagaa acatgaagtt acactatgtt gctgtgctta ctctagccat    180
cctgatgttc ctgacatggc ttccagaatc actgagctgt aacaaagcac tctgtgctag    240
tgatgtgagc aaatgcctca ttcaggagct ctgccagtgc cggccgggag aaggcaattg    300
ctcctgctgt aaggagtgca tgctgtgtct tggggccctt tgggacgagt gctgtgactg    360
tgttggtatg tgtaatcctc gaaattatag tgacacacct ccaacttcaa agagcacagt    420
ggaggagctg catgaaccga tcccttctct cttccgggca ctcacagaag gagatactca    480
gttgaattgg aacatcgttt ctttccctgt gcagaagaa ctttcacatc atgagaatct    540
ggtttcattt ttagaaactg tgaaccagcc acaccaccag aatgtgtctg tccccagcaa    600
taatgttcac gcgccttatt ccagtgacaa agaacacatg tgtactgtgg tttattttga    660
tgactgcatg tccatacatc agtgtaaaat atcctgtgag tccatgggag catccaaata    720
tcgctggttt cataatgcct gctgcgagtg cattggtcca gaatgtattg actatgtag    780
taaaactgtc aaatgtatga actgcatgtt ttaaagaaga caaatgcaaa ccaaagcaac    840
ttagtaaaat aataggtata aaaagttaaa aaaa                                874

<210> SEQ ID NO 4
<211> LENGTH: 223
<212> TYPE: PRT
<213> ORGANISM: homo sapien

<400> SEQUENCE: 4

Met Lys Leu His Tyr Val Ala Val Leu Thr Leu Ala Ile Leu Met Phe
 1               5                  10                  15
```

```
Leu Thr Trp Leu Pro Glu Ser Leu Ser Cys Asn Lys Ala Leu Cys Ala
         20                  25                  30

Ser Asp Val Ser Lys Cys Leu Ile Gln Glu Leu Cys Gln Cys Arg Pro
             35                  40                  45

Gly Glu Gly Asn Cys Ser Cys Cys Lys Glu Cys Met Leu Cys Leu Gly
 50                  55                  60

Ala Leu Trp Asp Glu Cys Cys Asp Cys Val Gly Met Cys Asn Pro Arg
 65                  70                  75                  80

Asn Tyr Ser Asp Thr Pro Pro Thr Ser Lys Ser Thr Val Glu Glu Leu
                 85                  90                  95

His Glu Pro Ile Pro Ser Leu Phe Arg Ala Leu Thr Glu Gly Asp Thr
            100                 105                 110

Gln Leu Asn Trp Asn Ile Val Ser Phe Pro Val Ala Glu Glu Leu Ser
            115                 120                 125

His His Glu Asn Leu Val Ser Phe Leu Glu Thr Val Asn Gln Pro His
130                 135                 140

His Gln Asn Val Ser Val Pro Ser Asn Asn Val His Ala Pro Tyr Ser
145                 150                 155                 160

Ser Asp Lys Glu His Met Cys Thr Val Val Tyr Phe Asp Asp Cys Met
                165                 170                 175

Ser Ile His Gln Cys Lys Ile Ser Cys Glu Ser Met Gly Ala Ser Lys
            180                 185                 190

Tyr Arg Trp Phe His Asn Ala Cys Cys Glu Cys Ile Gly Pro Glu Cys
            195                 200                 205

Ile Asp Tyr Gly Ser Lys Thr Val Lys Cys Met Asn Cys Met Phe
            210                 215                 220

<210> SEQ ID NO 5
<211> LENGTH: 3441
<212> TYPE: DNA
<213> ORGANISM: homo sapien

<400> SEQUENCE: 5
cggacgcgtg ggcggacgcg tgggcccgcs gcaccgcccc cggcccggcc ctccgccctc      60
cgcactcgcg cctccctccc tccgcccgct cccgcgccct cctccctccc tcctccccag     120
ctgtcccgtt cgcgtcatgc cgagcctccc ggccccgccg gccccgctgc tgctcctcgg     180
gctgctgctg ctcggctccc ggccggcccg cggcgccggc ccagagcccc ccgtgctgcc     240
catccgttct gagaaggagc cgctgcccgt tcggggagcg gcaggctgca ccttcggcgg     300
gaaggtctat gccttggacg agacgtggca cccggaccta gggcagccat cgggggtgat     360
gcgctgcgtg ctgtgcgcct gcgaggcgcc tcagtggggt cgccgtacca ggggccctgg     420
cagggtcagc tgcaagaaca tcaaaccaga gtgcccaacc ccggcctgtg ggcagccgcg     480
ccagctgccg ggacactgct gccagacctg ccccaggag cgcagcagtt cggagcggca     540
gccgagcggc ctgtccttcg agtatccgcg ggacccggag catcgcagtt atagcgaccg     600
cggggagcca ggcgctgagg agcggggccc tggtgacggc cacacggact tcgtggcgct     660
gctgacaggg ccgaggtcgc aggcggtggc acgagcccga gtctcgctgc tgcgctctag     720
cctccgcttc tctatctcct acaggcggct ggaccgccct accaggatcc gcttctcaga     780
ctccaatggc agtgtcctgt ttgagcaccc tgcagccccc acccaagatg gcctggtctg     840 tgggggtgtgg cgggcagtgc ctcggttgtc tctgcggctc cttagggcag aacagctgca     900
tgtggcactt gtgacactca ctcacccctt aggggaggtc tggggccctc tcatccggca     960
```

```
ccgggccctg gctgcagaga ccttcagtgc catcctgact ctagaaggcc ccccacagca    1020
gggcgtaggg ggcatcaccc tgctcactct cagtgacaca gaggactcct tgcattttt    1080 gctgctcttc cgagggctgc tggaacccag gagtggggga ctaacccagg ttcccttgag    1140
gctccagatt ctacaccagg ggcagctact gcgagaactt caggccaatg tctcagccca    1200
ggaaccaggc tttgctgagg tgctgcccaa cctgacagtc caggagatgg actggctggt    1260 gctggggag ctgcagatgg ccctggagtg ggcaggcagg ccagggctgc gcatcagtgg    1320
acacattgct gccaggaaga gctgcgacgt cctgcaaagt gtcctttgtg gggctgatgc    1380
cctgatccca gtccagacgg gtgctgccgg ctcagccagc ctcacgctgc taggaaatgg    1440
ctccctgatc tatcaggtgc aagtggtagg acaagcagt gaggtggtgg ccatgacact    1500
ggagaccaag cctcagcgga gggatcagcg cactgtcctg tgccacatgg ctggactcca    1560
gccaggagga cacacggccg tgggtatctg ccctgggctg ggtgcccgag ggctcatat    1620 gctgctgcag aatgagctct tcctgaacgt gggcaccaag gacttcccag acggagagct    1680
tcgggggcac gtggctgccc tgccctactg tgggcatagc gcccgccatg acacgctgcc    1740
cgtgccccta gcaggagccc tggtgctacc ccctgtgaag agccaagcag cagggcacgc    1800
ctggctttcc ttggataccc actgtcacct gcactatgaa gtgctgctgg ctgggcttgg    1860
tggctcagaa caaggcactg tcactgccca cctccttggg cctcctggaa cgccagggcc    1920
tcggcggctg ctgaagggat tctatggctc agaggcccag ggtgtggtga aggacctgga    1980 gccgaactg ctgcggcacc tggcaaaagg catggcctcc ctgatgatca ccaccaaggg    2040
tagccccaga ggggagctcc gagggcaggt gcacatagcc aaccaatgtg aggttggcgg    2100
actgcgcctg gaggcggccg gggccgaggg ggtgcgggcg ctggggggctc cggatacagc    2160 ctctgctgcg ccgcctgtgg tgcctggtct cccggcccta gcgcccgcca aacctggtgg    2220
tcctgggcgg ccccgagacc ccaacacatg cttcttcgag gggcagcagc gcccccacgg    2280
ggctcgctgg gcgcccaact acgacccgct ctgctcactc tgcacctgcc agagacgaac    2340
ggtgatctgt gacccggtgg tgtgcccacc gcccagctgc ccacacccgg tgcaggctcc    2400
cgaccagtgc tgccctgttt gccctgagaa acaagatgtc agagacttgc cagggctgcc    2460
aaggagccgg gacccaggag agggctgcta ttttgatggt gaccggagct ggcgggcagc    2520
gggtacgcgc tggcaccccg ttgtgccccc ctttggctta attaagtgtg ctgtctgcac    2580
ctgcaagggg ggcactggag aggtgcactg tgagaaggtg cagtgtcccc ggctggcctg    2640
tgcccagcct gtgcgtgtca accccaccga ctgctgcaaa cagtgtccag tggggtcggg    2700
ggcccacccc cagctggggg accccatgca ggctgatggg ccccggggct gccgttttgc    2760
tgggcagtgg ttcccagaga gtcagagctg gcacccctca gtgcccctt ttggagagat    2820 gagctgtatc acctgcagat gtggggcagg ggtgcctcac tgtgagcggg atgactgttc    2880
actgccactg tcctgtggct cggggaagga gagtcgatgc tgttcccgct gcacggccca    2940
ccggcggccc ccagagacca gaactgatcc agagctggag aaagaagccg aaggctctta    3000
gggagcagca gagggccaa gtgaccaaga ggatggggcc tgagctgggg aagggtggc    3060 atcgaggacc ttcttgcatt ctcctgtggg aagcccagtg cctttgctcc tctgtcctgc    3120
ctctactccc accccactca cctctgggaa ccacagctcc acaaggggga gaggcagctg    3180
ggccagaccg aggtcacagc cactccaagt cctgccctgc caccctcggc ctctgtcctg    3240
gaagccccac ccctttcctc ctgtacataa tgtcactggc ttgttgggat ttttaattta    3300
tcttcactca gcaccaaggg cccccgacac tccactcctg ctgcccctga gctgagcaga    3360
```

```
gtcattattg gagagttttg tatttattaa aacatttctt tttcagtcaa aaaaaaaaaa    3420
aaaaaaaaaa aaaaaaaaaa a                                              3441

<210> SEQ ID NO 6
<211> LENGTH: 954
<212> TYPE: PRT
<213> ORGANISM: homo sapien

<400> SEQUENCE: 6

Met Pro Ser Leu Pro Ala Pro Pro Ala Pro Leu Leu Leu Gly Leu
1               5                  10                  15

Leu Leu Leu Gly Ser Arg Pro Ala Arg Gly Ala Gly Pro Glu Pro
            20                  25                  30

Val Leu Pro Ile Arg Ser Glu Lys Glu Pro Leu Pro Val Arg Gly Ala
            35                  40                      45

Ala Gly Cys Thr Phe Gly Gly Lys Val Tyr Ala Leu Asp Glu Thr Trp
        50                  55                  60

His Pro Asp Leu Gly Gln Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110

Gln Pro Arg Gln Leu Pro Gly His Cys Cys Gln Thr Cys Pro Gln Glu
        115                 120                 125

Arg Ser Ser Ser Glu Arg Gln Pro Ser Gly Leu Ser Phe Glu Tyr Pro
    130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
            260                 265                 270

Ile Arg His Arg Ala Leu Ala Ala Glu Thr Phe Ser Ala Ile Leu Thr
        275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350

Ser Ala Gln Glu Pro Gly Phe Ala Glu Val Leu Pro Asn Leu Thr Val
        355                 360                 365
```

```
Gln Glu Met Asp Trp Leu Val Leu Gly Glu Leu Gln Met Ala Leu Glu
    370                 375                 380

Trp Ala Gly Arg Pro Gly Leu Arg Ile Ser Gly His Ile Ala Ala Arg
385                 390                 395                 400

Lys Ser Cys Asp Val Leu Gln Ser Val Leu Cys Gly Ala Asp Ala Leu
                    405                 410                 415

Ile Pro Val Gln Thr Gly Ala Ala Gly Ser Ala Ser Leu Thr Leu Leu
                420                 425                 430

Gly Asn Gly Ser Leu Ile Tyr Gln Val Gln Val Val Gly Thr Ser Ser
            435                 440                 445

Glu Val Val Ala Met Thr Leu Glu Thr Lys Pro Gln Arg Arg Asp Gln
450                 455                 460

Arg Thr Val Leu Cys His Met Ala Gly Leu Gln Pro Gly Gly His Thr
465                 470                 475                 480

Ala Val Gly Ile Cys Pro Gly Leu Gly Ala Arg Gly Ala His Met Leu
                    485                 490                 495

Leu Gln Asn Glu Leu Phe Leu Asn Val Gly Thr Lys Asp Phe Pro Asp
                500                 505                 510

Gly Glu Leu Arg Gly His Val Ala Leu Pro Tyr Cys Gly His Ser
            515                 520                 525

Ala Arg His Asp Thr Leu Pro Val Pro Leu Ala Gly Ala Leu Val Leu
530                 535                 540

Pro Pro Val Lys Ser Gln Ala Ala Gly His Ala Trp Leu Ser Leu Asp
545                 550                 555                 560

Thr His Cys His Leu His Tyr Glu Val Leu Leu Ala Gly Leu Gly Gly
                    565                 570                 575

Ser Glu Gln Gly Thr Val Thr Ala His Leu Leu Gly Pro Pro Gly Thr
                580                 585                 590

Pro Gly Pro Arg Arg Leu Leu Lys Gly Phe Tyr Gly Ser Glu Ala Gln
            595                 600                 605

Gly Val Val Lys Asp Leu Glu Pro Glu Leu Leu Arg His Leu Ala Lys
610                 615                 620

Gly Met Ala Ser Leu Met Ile Thr Thr Lys Gly Ser Pro Arg Gly Glu
625                 630                 635                 640

Leu Arg Gly Gln Val His Ile Ala Asn Gln Cys Glu Val Gly Gly Leu
                    645                 650                 655

Arg Leu Glu Ala Ala Gly Ala Glu Gly Val Arg Ala Leu Gly Ala Pro
                660                 665                 670

Asp Thr Ala Ser Ala Ala Pro Pro Val Val Pro Gly Leu Pro Ala Leu
            675                 680                 685

Ala Pro Ala Lys Pro Gly Pro Gly Arg Pro Arg Asp Pro Asn Thr
690                 695                 700

Cys Phe Phe Glu Gly Gln Gln Arg Pro His Gly Ala Arg Trp Ala Pro
705                 710                 715                 720

Asn Tyr Asp Pro Leu Cys Ser Leu Cys Thr Cys Gln Arg Arg Thr Val
                    725                 730                 735

Ile Cys Asp Pro Val Val Cys Pro Pro Pro Ser Cys Pro His Pro Val
                740                 745                 750

Gln Ala Pro Asp Gln Cys Cys Pro Val Cys Pro Glu Lys Gln Asp Val
            755                 760                 765

Arg Asp Leu Pro Gly Leu Pro Arg Ser Arg Asp Pro Gly Glu Gly Cys
770                 775                 780

Tyr Phe Asp Gly Asp Arg Ser Trp Arg Ala Ala Gly Thr Arg Trp His
```

```
                    785                 790                 795                 800
Pro Val Val Pro Pro Phe Gly Leu Ile Lys Cys Ala Val Cys Thr Cys
                805                 810                 815

Lys Gly Gly Thr Gly Glu Val His Cys Glu Lys Val Gln Cys Pro Arg
                820                 825                 830

Leu Ala Cys Ala Gln Pro Val Arg Val Asn Pro Thr Asp Cys Cys Lys
            835                 840                 845

Gln Cys Pro Val Gly Ser Gly Ala His Pro Gln Leu Gly Asp Pro Met
        850                 855                 860

Gln Ala Asp Gly Pro Arg Gly Cys Arg Phe Ala Gly Gln Trp Phe Pro
865                 870                 875                 880

Glu Ser Gln Ser Trp His Pro Ser Val Pro Pro Phe Gly Glu Met Ser
                885                 890                 895

Cys Ile Thr Cys Arg Cys Gly Ala Gly Val Pro His Cys Glu Arg Asp
                900                 905                 910

Asp Cys Ser Leu Pro Leu Ser Cys Gly Ser Gly Lys Glu Ser Arg Cys
            915                 920                 925

Cys Ser Arg Cys Thr Ala His Arg Arg Pro Pro Glu Thr Arg Thr Asp
    930                 935                 940

Pro Glu Leu Glu Lys Glu Ala Glu Gly Ser
945                 950
```

BONE MORPHOGENETIC PROTEIN ANTAGONIST AND USES THEREOF

Tissue microenvironments play a critical role in specifying cellular niches in both the developing embryo and adult organisms. In development, cell fate decisions are dictated not only by cell-autonomous signals but also by stimuli from the surrounding tissue microenvironment. Similarly, in adult tissues that continue to renew throughout the lifetime of the organism, such as the skin, intestinal epithelium, and hematopoietic system, the self renewal and maturation of the stem cell population are regulated by specific molecular cues derived from the corresponding microenvironments. In the skin, hair follicle morphogenesis is regulated by signals coming from the dermal papilla, a specialized mesenchymal structure that signals to matrix stem cells located across the basement membrane. Similarly, the modulation of stem cell activity in the intestine is also subject to cues derived from underlying mesenchymal cells that surround the crypt. Hematopoietic stem cells are regulated in part by osteoblasts, cells that reside in the adjacent bone spicule. In all of these cases, a crucial feature of the regulation of stem cell compartment size, location, and timing of self renewal is the production of critical factors by a specialized set of mesenchymal cells that create a customized microenvironment.

During carcinogenesis, an analogous system of specialized tissue microenvironment cells may also be important in specifying a "tumor cell niche" that supports a self-renewing population of tumor cells. Paradoxically, although uncontrolled proliferation and survival are the cardinal characteristics of cancer cells, it can be difficult to sustain these cells away from their corresponding microenvironment, either in culture or as explants. While a cell becomes malignant as a result of changes to its genetic material, the neoplastic cancer cell is only part of the story in cancer development. As a cancer cell grows within the architecture of the body's tissues and organs, it interacts with its surrounding environment.

Mounting evidence now suggests that a dynamic interaction occurs between the cancer cell and its microenvironment, with each profoundly influencing the behavior of the other. This "tumor microenvironment," is populated with a variety of different cell types, is rich in growth factors and enzymes, and includes parts of the blood and lymphatic systems. It promotes some of the most destructive characteristics of cancer cells and permits the tumor to grow and spread. Genetic studies have shown that stromal cells are altered in some inherited cancer susceptibility syndromes. In breast cancer, rearrangements at several loci have been noted exclusively in tumor-associated stromal cells. In vivo and in vitro experiments demonstrated that human prostatic epithelial cells showed dramatic changes both in histology and growth rate when grown with human fibroblast cells derived from prostatic carcinoma, suggesting that carcinoma-derived fibroblasts can stimulate tumorigenesis. Others have shown that co-injection of fibroblasts with tumor epithelial cells into mice can enhance tumor formation. Evidence suggests that the interaction between cancer cells and their microenvironment is key to this transition from transformed cell to a tumor mass. It has been observed that the influence between the environment and tumor cells is bi-directional. Non-cancerous cells that adjoin a cancerous tumor often take on atypical characteristics and exert a profound influence on a cancer cell's ability to develop into a tumor.

Carcinomas are histologically complex tissues comprising not only tumor cells, but also fibroblasts, smooth muscle cells, endothelial cells, adipose cells, and leukocytes, as well as components of the extracellular matrix. Multiple lines of evidence in recent years have suggested that interactions with these cells and factors in the tumor microenvironment, or tumor cell niche, may also play a critical role in the initiation and progression of cancer. It is becoming evident that events outside the cancer cell are as important to disease development as the disrupted processes inside the cell. This broadened concept of cancer requires an understanding of stromal cells, and the interplay between the cancer cell and its immediate environment. This new perspective may also open new avenues to treatment. Rather than targeting the cancer cell alone, new treatment approaches can potentially target the features of the microenvironment that allow tumors to develop and progress. In addition, because the microenvironment often exerts considerable influence over tumor cells in the early stages of tumor development, it promises to be an attractive target for prevention efforts. The present invention addresses this issue.

SUMMARY OF THE INVENTION

The present invention provides novel methods and reagents for specifically targeting tumor-associated stromal cells for therapeutic, diagnostic and imaging purposes, using agents specific for secreted antagonists of the bone morphogenetic protein (BMP) pathway, including Gremlin1, TSG1 and Chordin. These targets have been identified by the applicants as being overexpressed in tumor-associated stromal cells, and thus allow for the selective inhibition of cell function, diagnosis of tumor association, or selective marking for visualization with therapeutic or visualizing compositions that have a specific affinity for these protein targets. Expression is highly specific to the stromal cells. Tumors of interest include, without limitation, carcinomas, e.g. basal cell carcinomas, carcinomas of the bladder, breast, lung, colon pancreas, esophagus, prostate, head and neck, and the like. It is shown herein that varied carcinomas have a commonality in stromal cell components, even where there is not a commonality in the neoplastic epithelial cell component.

Agents specific for secreted antagonists of the bone morphogenetic protein (BMP) pathway, including Gremlin1, TSG1 and Chordin, are useful in the treatment of tumors in patients. In particular it is shown herein that Gremlin1 can effectively overcome BMP inhibition of cell proliferation and differentiation of tumor cells, and that tumor-associated stromal cells express Gremlin1. In some embodiments, the methods comprise administering an effective amount of a composition comprising an agent specific for Gremlin1, which agent inhibits the activity of Gremlin1. Agents of interest include small molecule inhibitors, antibodies, anti-sense RNA, RNAi, and the like. Administration of the therapeutic composition may be by any acceptable means. In some embodiments of the invention, combined therapies are provided, where administration of an agent targeted to the tumor cells is combined with administration of an agent targeted to the BMP antagonist.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8. GREMLIN 1 RNA is expressed in tumor, but not nontumor, lung tissue from the same patient. ISH for GREMLIN 1 RNA was performed on large sections of lung containing tumor and nontumor tissues from the same patients. Representative images from one patient are shown. GREMLIN 1 RNA is represented by punctate brown dots, and nuclei are counterstained with Hematoxylin.

DETAILED DESCRIPTION OF THE EMBODIMENTS

Figure 1:
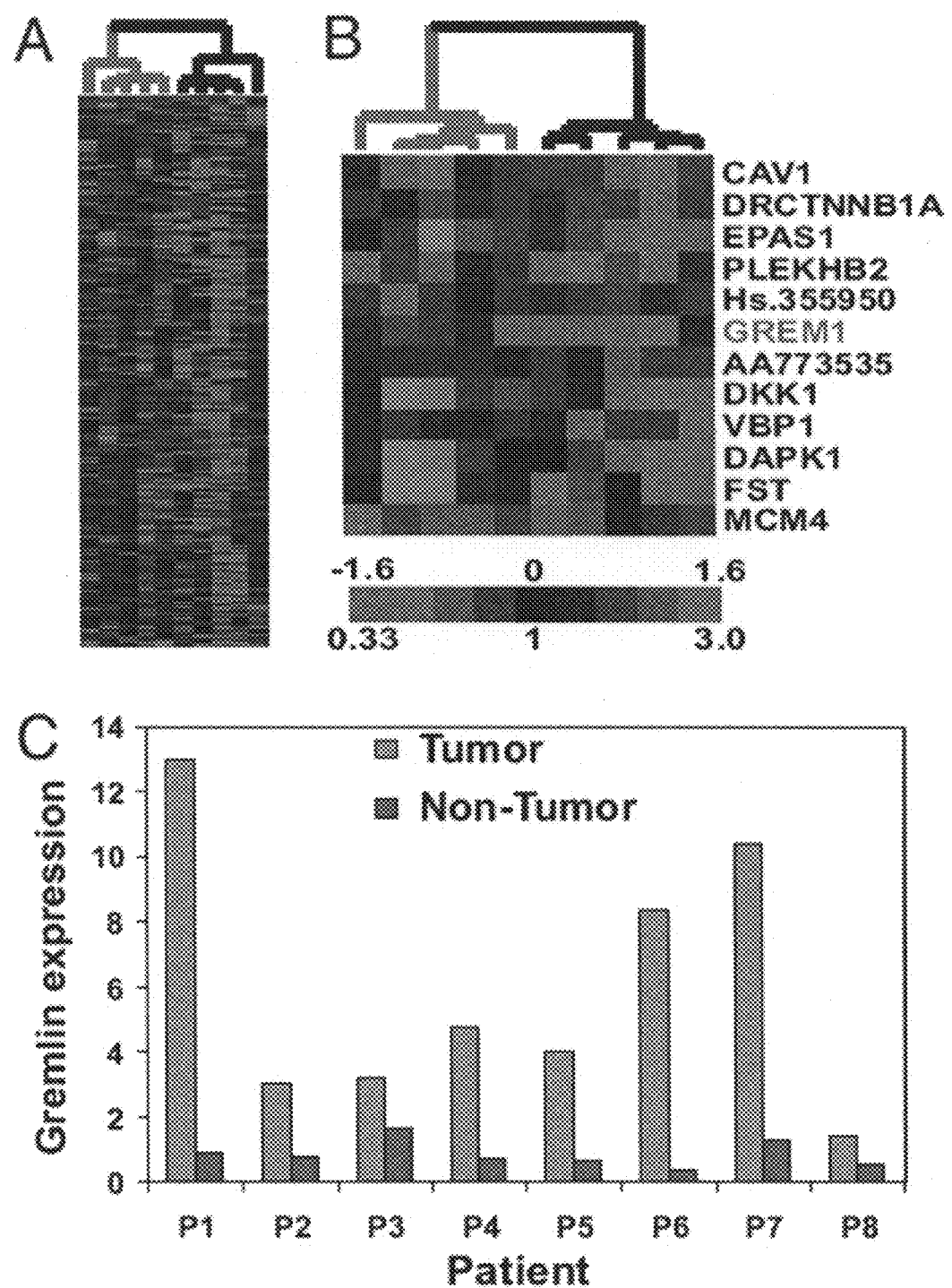
FIG. 1. GREMLIN 1 mRNA is elevated in BCC tumor-derived stromal cultures ex vivo and in BCC tumors in vivo. (A and B) Gene expression in stromal cells from BCC tumor and nontumor skin. Each row in the heat map represents a gene, and each column represents a sample; cultures derived from BCC and nontumor skin are indicated by red and black branches, respectively. (A) Hierarchical clustering of samples based on expression of 403 array elements selected for differential expression by two-class Significance Analysis of Microarrays analysis at a false discovery rate of 15%. The level of expression of each gene in each stromal cell sample is relative to the mean level of expression of that gene across all samples and is represented by using a red-green color scale. (B) Hierarchical clustering of samples according to their expression of a more stringently selected set of genes (false discovery rate of 5%). (C) RT-PCR analysis of whole-tissue samples of BCC tumor or adjacent nontumor skin from eight patients. The relative level of GREMLIN 1 RNA in each sample was normalized to GAPDH for that sample.

Applicants have identified secreted antagonists of the BMP pathway, including Gremlin1, TSG1 and Chordin, as being differentially regulated between tumor-associated stromal cells and normal tissue. Cancers shown to have differential expression include a number of solid tumors, particularly carcinomas. Applicants have performed differential expression analysis between tumor-associated and normal stromal cells, and have identified the Gremlin1 and other BMP antagonists as being specifically expressed by the stromal cell component of the tumors. The overexpressed Gremlin genes and protein products mediate the maintenance of tumors. Agents that block Gremlin, or that prevent expression are useful as therapeutic agents to inhibit growth signaling to the tumor cells.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The invention finds use in the prevention, treatment, detection or research into solid cancers, particularly carcinomas. Carcinomas are malignancies that originate in the epithelial tissues. Epithelial cells cover the external surface of the body, line the internal cavities, and form the lining of glandular tissues. In adults, carcinomas are the most common forms of cancer. Carcinomas include the a variety of adenocarcinomas, for example in prostate, lung, etc.; adrenocortical carcinoma; hepatocellular carcinoma; renal cell carcinoma, ovarian carcinoma, carcinoma in situ, ductal carcinoma, carcinoma of the breast, basal cell carcinoma; squamous cell carcinoma; transitional cell carcinoma; colon carcinoma; nasopharyngeal carcinoma; multilocular cystic renal cell carcinoma; oat cell carcinoma, large cell lung carcinoma; small cell lung carcinoma; etc. Carcinomas may be found in prostrate, pancreas, colon, brain (usually as secondary metastases), lung, breast, skin, etc.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

Based on the differential expression described herein, Gremlin was selected as a prime target for selective therapeutic agents. Gremlin is an antagonist of bone morphogenetic protein (BMP) signaling that is expressed in the neural crest. Gremlin belongs to a gene family that includes the head-inducing factor Cerberus and the tumor suppressor DAN. All family members are secreted proteins and that they act as BMP antagonists. It is believed the Gremlin binds BMPs, preventing them from interacting with their receptors. For example, see Hsu et al. (1998) *Molec. Cell* 1: 673-683; Khokha et al. (2003) *Nature Genet.* 34: 303-307; and Topol et al. (2000) *Cytogenet. Cell Genet.* 89: 79-84, each herein specifically incorporated by reference.

For convenience, the sequence of human Gremlin 1 is provided herein as SEQ ID NO:1 (polynucleotide) and SEQ ID NO:2 (polypeptide). The sequence of human TSG1 is provided herein as SEQ ID NO:3 (polynucleotide) and SEQ ID NO:4 (polypeptide). The sequence of human Chordin is provided herein as SEQ ID NO:5 (polynucleotide) and SEQ ID NO:6 (polypeptide).

Nucleic Acids

The sequences of BMP antagonists, including Gremlin, find use in diagnostic and therapeutic methods, for the recombinant production of the encoded polypeptide, and the like. The nucleic acids of the invention include nucleic acids having a high degree of sequence similarity or sequence identity to the common, or wild-type sequences. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707, 829. Nucleic acids that are substantially identical to the provided nucleic acid sequence, e.g. allelic variants, genetically altered versions of the gene, etc., bind the common, or wild-type sequences under stringent hybridization conditions. Further specific guidance regarding the preparation of nucleic acids is provided by Fleury et al., (1997) *Nature Genetics* 15:269-272; Tartaglia et al., PCT Publication No. WO 96/05861; and Chen et al., PCT Publication No. WO 00/06087, each of which is incorporated herein in its entirety.

The genes provided in the sequence listing may be obtained using various methods well known to those skilled in the art, including but not limited to the use of appropriate probes to detect the genes within an appropriate cDNA or genomic DNA library, antibody screening of expression libraries to detect cloned DNA fragments with shared structural features, direct chemical synthesis, and amplification protocols. Libraries are preferably prepared from glioblastoma versus normal cells. Cloning methods are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1-3, Cold Spring Harbor Laboratory, Cold Spring Harbor Press, NY; and Current Protocols (1994), a joint venture between Greene Publishing Associates, Inc. and John Wiley and Sons, Inc.

The nucleic acids can be cDNAs or genomic DNAs, as well as fragments thereof. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear. RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5', or internal regulatory sequences as sometimes found in introns, contains sequences required for proper tissue, stage-specific, or disease-state specific expression, and are useful for investigating the up-regulation of expression in tumor cells.

Probes, antisense oligonucleotides, RNAi, expression vectors, and the like specific to the nucleic acids provided herein can be readily generated. Probes and oligonucleotides are usually at least about 18 nt, 25 nt, 50 nt or more of the corresponding contiguous sequence of one of the provided sequences, and are usually less than about 2, 1, or 0.5 kb in length. Preferably, probes are designed based on a contiguous sequence that remains unmasked following application of a masking program for masking low complexity. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides

Polypeptides encoded by BMP antagonist genes are of interest for screening methods, as reagents to raise antibodies, and the like. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the common, or wild-type polypeptide.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a BMP ANTAGONIST protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

For various purposes, for example as an immunogen, the entire BMP antagonist polypeptide or a fragment derived therefrom may be used. Preferably, one or more 8, 10, 20, 30 amino acid peptide portions, e.g. of an extracellular domain may be utilized.

Specific Binding Members

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. For the purposes of the present invention, the two binding members may be known to associate with each other, for example where an assay is directed at detecting compounds that interfere with the association of a known binding pair. Alternatively, candidate compounds suspected of being a binding partner to a compound of interest may be used.

Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; lipid and lipid-binding protein; etc. The specific binding pairs may include analogs, derivatives and fragments of the original specific binding member. For example, a receptor and ligand pair may include peptide fragments, chemically synthesized peptidomimetics, labeled protein, derivatized protein, etc.

In a preferred embodiment, the specific binding member is an antibody. Antibodies that bind specifically to one of the Bmp antagonist proteins and thereby block or inhibit the activity are of particular interest. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

All types of immunoglobulins, IgG, e.g. IgG1, IgG2a, IgG2b, IgG3, IgG4, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a BMP antagonist antigen comprising an antigenic portion of the polypeptide is initially injected into any of a wide variety of mammals (e.g., mice, rats, rabbits, sheep or goats). Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. Many such cell lines (such as myelomas) are known to those skilled in the art.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody are preferred for use in the invention. Thus, humanized, single chain, chimeric, or human antibodies, which produce less of an immune response when administered to humans, are preferred for use in the present invention.

Antibody fragments that recognize specific epitopes may be generated by techniques well known in the field. These fragments include, without limitation, F(ab')$_2$ fragments, which can be produced by pepsin digestion of the antibody molecule, and Fab fragments, which can be generated by reducing the disulfide bridges of the F(ab')$_2$ fragments.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the brain tumor protein targets, although the term will encompass all immunoglobulins, derivatives, fragments, recombinant or engineered immunoglobulins, and modified immunoglobulins, as described above.

Candidate antibodies can be tested for by any suitable standard means, e.g. ELISA assays, etc. As a first screen, the antibodies may be tested for binding against the immunogen. As a second screen, candidates may be tested for binding to an appropriate stromal cell line, or to primary tumor tissue samples. For these screens, the candidate antibody may be labeled for detection. After selective binding is established, the candidate antibody, or an antibody conjugate produced as described below, may be tested for appropriate activity (i.e., the ability to decrease tumor cell growth) in an in vivo model, such as an appropriate tumor culture system, or in an animal model. The binding affinity of the antibody may be determined using Biacore SPR technology, as is known in the art.

Antibodies that alter the biological activity of a BMP antagonist may be assayed in functional formats, such as cell culture or mouse/rat tumor model studies. The ability of the tumor cells to grow in the presence of stromal cells and a candidate antibody is then determined.

Diagnostic and Prognostic Methods

The differential expression of BMP antagonist genes and/or gene products in tumor-associated stromal cells indicates that these can serve as markers for diagnosis, for imaging, as well as for therapeutic applications. In general, such diagnostic methods involve detecting an elevated level of expression of BMP antagonist gene transcripts or gene products in the cells or tissue of an individual or a sample therefrom. A variety of different assays can be utilized to detect an increase in gene expression, including both methods that detect gene transcript and protein levels. More specifically, the diagnostic and prognostic methods disclosed herein involve obtaining a sample from an individual and determining at least qualitatively, and preferably quantitatively, the level of a BMP antagonist gene product expression in the sample. Usually this determined value or test value is compared against some type of reference or baseline value.

Nucleic acids or binding members such as antibodies that are specific for polypeptides derived from the sequence of one of the provided sequences are used to screen patient samples for increased expression of the corresponding mRNA or protein. Samples can be obtained from a variety of sources. Samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from extracellular fluids for the detection of secreted proteins, such as Gremlin, or tumor biopsy samples that include stromal cells. Also included in the term are derivatives and fractions of such cells and fluids. Samples can also be derived from in vitro cell cultures, including the growth medium, recombinant cells and cell components. Diagnostic samples are collected from an individual that has, or is suspected to have, a carcinoma. The presence of specific markers is useful in identifying and staging the tumor.

Nucleic Acid Screening Methods

Some of the diagnostic and prognostic methods that involve the detection of a BMP antagonist gene transcript begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. Nos. 5,210,015 to Gelfand, 5,538,848 to Livak, et al., and 5,863,736 to Haaland, each of which is incorporated by reference in its entirety.

Polypeptide Screening Methods

Screening for expression of the subject sequences may be based on the functional or antigenic characteristics of the protein. Various immunoassays designed to detect polymorphisms in proteins encoded by the sequences corresponding to the provided sequences may be used in screening. Detection may utilize staining of extracellular fluids, cells or histological sections, performed in accordance with conventional methods, using antibodies or other specific binding members that specifically bind to the BMP antagonist polypeptides. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and polypeptide is serum, plasma, extracellular fluid, and the like. Measuring the concentration of the target protein in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding. After incubation, the insoluble support is generally washed of non-bound components. After washing, a solution containing a second antibody is applied. The antibody will bind to one of the proteins of interest with sufficient specificity such that it can be distinguished from other components present. The second antibodies may be labeled to facilitate direct, or indirect quantification of binding. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the targeted polypeptide, conveniently using a labeling method as described for the sandwich assay.

In some cases, a competitive assay will be used. In addition to the patient sample, a competitor to the targeted protein is added to the reaction mix. The competitor and the target compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

Active Agents

Agents that modulate activity of BMP antagonist genes or proteins provide a point of therapeutic or prophylactic intervention, particularly agents that inhibit activity of the polypeptide or expression of the gene. Numerous agents are useful in inhibiting this activity, including agents that directly inhibit expression, e.g. antisense or RNAi specific for the targeted polypeptide; and agents that act on the protein, e.g. specific antibodies and analogs thereof as described above, small organic molecules that block binding activity, etc.

Antisense molecules can be used to down-regulate expression in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Compound screening may be performed using an in vitro model, a genetically altered cell or animal, tumor associated stromal cells expressing a BMP antagonist; purified protein corresponding to any one of the provided BMP antagonist genes; and the like. One can identify ligands or substrates that bind to or inhibit the action of the encoded polypeptide.

Polypeptides of interest for screening include those encoded by BMP antagonist genes, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by brain tumor associated genes, or a homolog thereof.

Compound screening identifies agents that inhibit activity, particularly inhibit binding activity, of the BMP antagonist polypeptides, including the binding of, fore example, Gremlin to a BMP protein. Of particular interest are screening assays for agents that have a low toxicity for human cells. A wide variety of assays may be used for this purpose. Knowledge of the 3-dimensional structure of the encoded protein, derived from crystallization of purified recombinant protein, could lead to the rational design of small drugs that specifically inhibit activity. These drugs may be directed at specific domains.

The effect of an agent on signaling pathways may be determined using reporter assays that well known in the art. Binding by a ligand triggers activation of key cell signaling pathways, such as Shh, wnt, BMP signaling, etc. implicated in tumors. The cis reporting system can be used to determine if the gene or protein of interest acts on specific enhancer elements while the trans-activator indicates if the gene or protein of interest directly or indirectly may be involved in the phosphorylation and activation of the transcription factor.

The term "agent" as used herein describes any molecule, e.g. protein or pharmaceutical, with the capability of altering or inhibiting the physiological function of a BMP antagonist polypeptide. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to a BMP antagonist polypeptide, as at least some of the compounds so identified are likely inhibitors. The binding assays usually involve contacting a BMP antagonist polypeptide with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Certain screening methods involve screening for a compound that modulates the expression of a BMP antagonist gene. Such methods generally involve conducting cell-based assays in which test compounds are contacted with one or more cells expressing a BMP antagonist gene and then detecting and an increase in expression. Some assays are performed with tumor-associated stromal cells that express endogenous BMP antagonist genes.

The level of expression or activity can be compared to a baseline value. As indicated above, the baseline value can be a value for a control sample or a statistical value that is representative of expression levels for a control population. Expression levels can also be determined for cells that do not express a BMP antagonist gene, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal or in a cell culture model, as described in the Examples, that serves as a model for humans and then determining if the protein or gene product is inhibited. The animal models utilized in validation studies generally are mammals. Specific examples of suitable animals include, but are not limited to, primates, mice, and rats.

Active test agents identified by the screening methods described herein that inhibit BMP antagonist polypeptide activity and/or tumor growth can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Pharmaceutical Formulations and Methods of Treatment

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, intracavity or direct injection in the tumor. Where the tumor is a solid tumor, the antibody may be administered by first creating a resection cavity in the location of the tumor.

The effective amount of a therapeutic composition to be given to a particular patient will depend on a variety of factors, several of which will be different from patient to patient. A competent clinician will be able to determine an effective amount of a therapeutic agent to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available, a clinician can determine the maximum safe dose for an individual, depending on the route of administration. Compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials. Typically the dosage will be 0.001 to 100 milligrams of agent per kilogram subject body weight.

The compositions can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke immune responses are preferred.

Combination Therapies

In some embodiments of the invention, a combination therapy is used, where an inhibitor of a BMP antagonist, which targets tumor-associated stromal cell, is administered in conjunction with a chemotherapeutic agent that targets tumor cells. Synergistic combinations provide for comparable or improved therapeutic effects, while lowering adverse side effects.

Chemotherapeutic, or anti-proliferative agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Such agents are used in the treatment of cancer. Antimetabolite agents include methotrexate, pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other natural products include azathioprine; brequinar; alkaloids and synthetic or semi-synthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithrmycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like. Hormone modulators include adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide. Estrogens stimulate proliferation and differentiation, therefore compounds that bind to the estrogen receptor are used to block this activity. Corticosteroids may inhibit T cell proliferation. Other chemotherapeutic agents include metal complexes, e.g. cisplatin (cis-DDP), carboplatin, etc.; ureas, e.g. hydroxyurea; and hydrazines, e.g. N-methylhydrazine. Other anti-proliferative agents of interest include immunosuppressants, e.g. mycophenolic acid, thalidomide, desoxyspergualin, azasporine, leflunomide, mizoribine, azaspirane (SKF 105685), etc., taxols, e.g. paclitaxel, etc.

The anti-BMP antagonist and chemotherapeutic agents can be incorporated into a variety of formulations for therapeutic administration. The anti-BMP antagonist and chemotherapeutic agent can be delivered simultaneously, or within a short period of time, by the same or by different routes. In one embodiment of the invention, a co-formulation is used, where the two components are combined in a single suspension. Alternatively, the two may be separately formulated. Part of the total dose may be administered by different routes. Such administration may use any route that results in systemic absorption, by any one of several known routes, including but not limited to inhalation, i.e. pulmonary aerosol administration; intranasal; sublingually; orally; and by injection, e.g. subcutaneously, intramuscularly, etc.

The following examples are offered by way of illustration and not by way of limitation.

EXAMPLE 1

Although tissue microenvironments play critical roles in epithelial development and tumorigenesis, the factors mediating these effects are poorly understood. In this work, we used a genomic approach to identify factors produced by cells in the microenvironment of basal cell carcinoma (BCC) of the skin, one of the most common human cancers. The global gene expression programs of stromal cell cultures derived from human BCCs showed consistent, systematic differences from those derived from non-tumor skin. The gene most consistently expressed at a higher level in BCC tumor stromal cells compared with those from non-tumor skin was GREMLIN 1, which encodes a secreted antagonist of the bone morphogenetic protein (BMP) pathway. BMPs and their antagonists are known to play a crucial role in stem and progenitor cell biology as regulators of the balance between expansion and differentiation. We found GREMLIN 1 expression in the stroma of human BCC tumors but not in normal skin in vivo. Furthermore, BMP 2 and 4 are expressed by BCC cells. Ex vivo, BMP inhibits, and Gremlin 1 promotes, proliferation of cultured BCC cells. We further found that GREMLIN 1 is expressed by stromal cells in many carcinomas but not in the corresponding normal tissue counterparts that we examined. Our data demonstrates that this BMP antagonist is an important constituent of tumor stroma, providing a favorable microenvironment for cancer cell survival and expansion in many cancers.

We cultured stromal cells from BCC tumor and non-tumor human skin and compared those two cell populations by cDNA microarray analysis. Antagonists of the bone morphogenetic protein (BMP) pathway were among the genes most consistently and significantly differentially expressed between the two populations. Given what is already known about the role of BMPs and their antagonists in regulating stem cell compartments in normal development and physiology, we hypothesized that a similar role could be played by BMPs and BMP antagonists in the context of the tumor.

Results

Identification of Stromal Factors Important for BCC Tumorigenesis. To identify factors produced by tumor-associated stromal cells that contribute to the initiation or maintenance of BCC, we cultured stromal cells from fresh samples of human BCC or non-tumor skin. The cells adhered readily to untreated plastic plates and were spindle-shaped and elongated. We used the Significance Analysis of Microarrays algorithm to identify genes differentially expressed between tumor- and non-tumor-associated stromal cells (FIG. 1A). Fourteen genes were identified at an estimated false discovery rate of 5%, with 13 genes expressed at higher levels and one gene expressed at a lower level in the tumor-associated cells (FIG. 1B and Table 1). Two of the 13 genes more highly expressed in BCC-derived stromal cells, GREM1 (GREMLIN 1) and FST (FOLLISTATIN), both encode antagonists of the BMP pathway.

TABLE 1

Genes that distinguish BCC- vs. nontumor-derived stromal cells

| IMAGE ID | Gene name | SAM score |
|---|---|---|
| Genes elevated in BCC- vs. nontumor-derived stromal cells | | |
| IMAGE: 1665349 | GREM1 | 2.7 |
| IMAGE: 131979 | EPAS1 | 2.7 |
| IMAGE: 869187 | EPAS1 | 2.5 |
| IMAGE: 324513 | GREM1 | 2.4 |
| IMAGE: 270786 | PLEKHB2 | 2.3 |
| IMAGE: 625740 | DRCTNNB1A | 2.3 |
| IMAGE: 669375 | DKK1 | 2.3 |
| IMAGE: 2043415 | DAPK1 | 2.2 |
| IMAGE: 1619049 | Hs.559527 | 2.2 |
| IMAGE: 1554314 | Chimeric clone | 2.1 |
| IMAGE: 844954 | AA773535 | 2.1 |

TABLE 1-continued

Genes that distinguish BCC- vs. nontumor-derived stromal cells

| IMAGE ID | Gene name | SAM score |
|---|---|---|
| IMAGE: 1534053 | Chimeric clone | 2.1 |
| IMAGE: 308060 | VBP1 | 2.0 |
| IMAGE: 841664 | CAV1 | 2.0 |
| IMAGE: 1883559 | FST | 2.0 |

Genes decreased in BCC- vs. nontumor-derived stromal cells

| IMAGE: 346257 | MCM4 | −2.8 |

Global gene expression patterns of five BCC-stromal cultures and five nontumor skin stromal cultures were characterized by DNA microarrays. Significance Analysis of Microarrays (SAM) was then used to identify a set of genes whose expression levels were significantly different between tumor- and nontumor-derived stromal cells at a false discovery rate of 5%. The clone identifier, gene name, and SAM score are listed.

Figure 2:
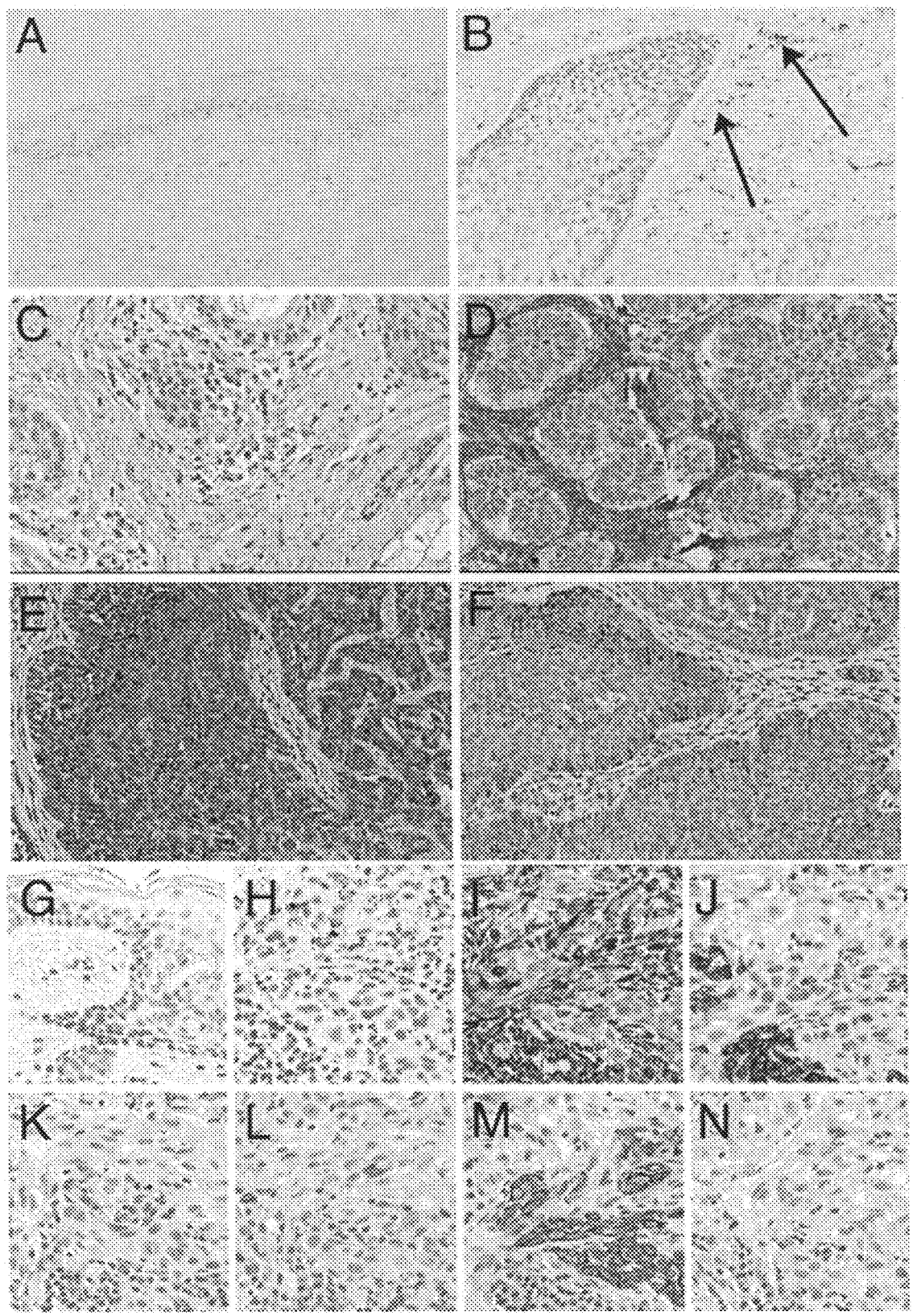
FIG. 2. Expression of GREMLIN 1 and BMP2 and 4 in BCC tumor tissues. (A and B) ISH for GREMLIN 1 RNA in normal scalp (A) and BCC tumor skin (B). GREMLIN 1 is expressed by stromal cells surrounding the tumor (indicated by arrows) but is undetectable in normal scalp. Positive signal appears as dark purple dots. (C and D) IHC for gremlin 1 protein in normal scalp (C) and BCC tumor skin (D). Positive signal appears as diffuse brown staining. (E and F) IHC with antibodies against BMP 2 (E) and 4 (F) in large sections of human BCC. Signal is represented by brown color. (G-N) serial sections of a BCC tumor showing that GREMLIN 1-expressing cells have properties of fibroblasts. (G and H) RNA ISH for GREMLIN 1 RNA in nontumor (G) and tumor (H) skin. GREMLIN 1 expression is indicated by dark purple dots. (I-N) IHC for cell lineage markers vimentin (I), CD45 (J), CD31 (K), desmin (L), pancytokeratin (M), and GFAP (N). Signal is represented by brown color.
Figure 6:
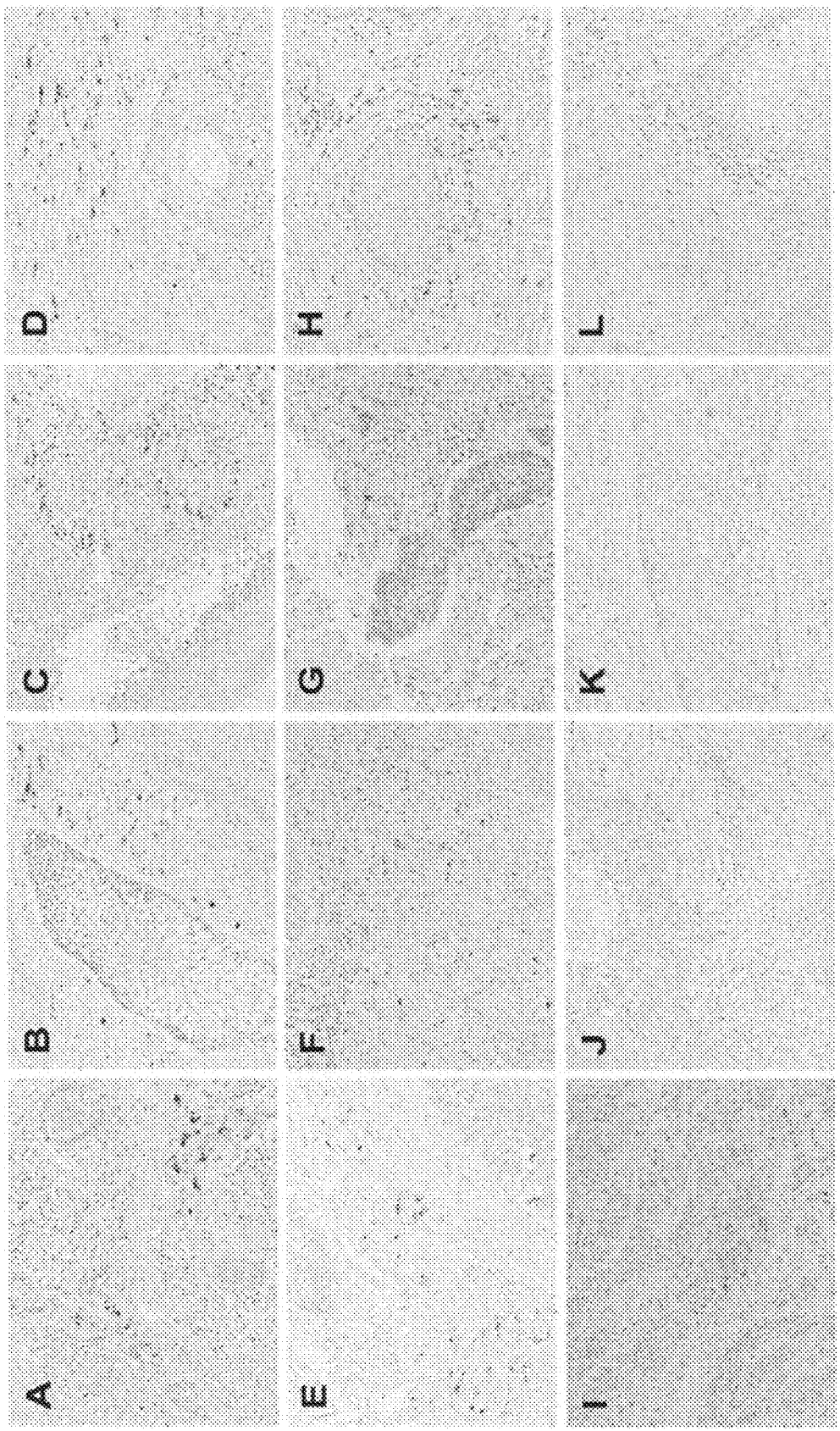
FIG. 6. GREMLIN 1 RNA is expressed in basal cell carcinoma (BCC) tumor stroma. Each image shows a representative image of in situ hybridization (ISH) for GREMLIN 1 in paraffin-embedded BCC tumors from a different patient. GREMLIN 1 is represented by punctate purple dots, and nuclei are counterstained with methyl green. Tumors positive (A-J) and negative (K and L) for GREMLIN 1.

GREMLIN 1 Expression Is Elevated in BCC, and BMPs Are Highly Expressed by BCC Tumors. We analyzed expression of GREMLIN 1 in vivo in human tissue by quantitative RT-PCR analysis of independent samples of whole tissue from eight matched BCC and adjacent non-tumor skin samples. GREMLIN 1 transcripts were, indeed, expressed at higher levels in BCC tissue than in adjacent non-tumor tissue from the same patient (FIG. 1C). We then performed in situ hybridization (ISH) in 15 paraffin embedded BCC tissue samples and found detectable GREMLIN 1 mRNA expression in 12 of 15 samples (80%). Expression was localized predominantly to stromal cells in the tumor, and immunohistochemistry (IHC) localized gremlin 1 protein to the stroma surrounding the tumor cell nests (FIGS. 2 B and D and FIG. 6). In contrast, no expression of GREMLIN 1 RNA or protein was detected in normal skin (FIGS. 2 A and C). Thirty-nine sections of normal skin from multiple anatomical sites, including arm (dorsal, ventral, posterior, and anterior), hand (dorsal and ventral), digits (posterior), palm, foot (dorsal and plantar), and leg (anterior, posterior, dorsal, and midline), were all negative for GREMLIN 1 RNA, with only two exceptions: a few stromal cells surrounding a neuromuscular junction in one section of skin from below the knee, and a small number of stromal cells deep in the dermis of the foot dorsum (data not shown). These results indicate that GREMLIN 1 RNA expression is below levels of detection or absent in the vast majority of normal human skin sites.

We found that BMP 2 and 4 are, indeed, expressed in BCC tumor nests (FIGS. 2 E and F), providing a source of BMP in BCC tumors that needs to be antagonized to promote proliferation of tumor cells. BMP antibody staining localized mostly to tumor cells, with macrophages occasionally demonstrating positive staining. To better characterize the stromal cell population that expressed GREMLIN 1 in BCC tumors, we analyzed adjacent serial sections of tumor by ISH for GREMLIN 1 and IHC for various cell lineage markers: vimentin (characteristic of mesenchymal cells), CD45 (hematopoietic lineage), CD31 (endothelial cells), desmin (smooth muscle cells), cytokeratins (epithelial cells), and, glial fibrillary acid protein (astrocytes and Schwann cells). GREMLIN 1-expressing cells were also strongly positive for vimentin, mostly or entirely negative for CD45 and desmin, and completely negative for CD31, keratins, and glial acid fibrillary protein (GFAP) (FIG. 2 G-N).

Figure 3:
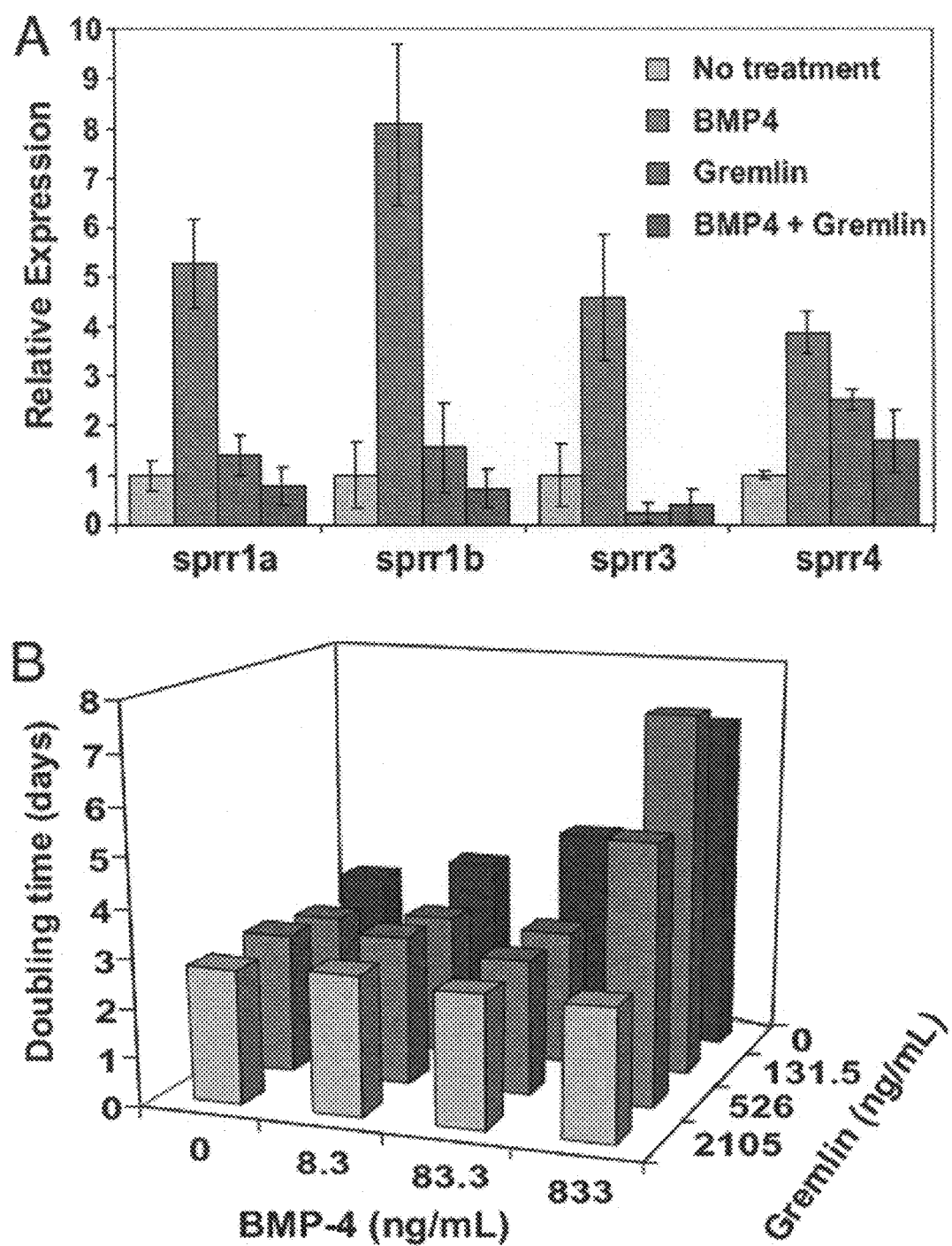
FIG. 3. Effects of BMP and gremlin 1 on BCC cell differentiation and expansion in vitro. (A) Cells were cultured from a human BCC tumor and then treated for 7 days in culture with recombinant human BMP 4 (833 ng/ml), recombinant mouse gremlin 1 ($2 \times 10^5$ ng/ml), or both. Populations were then compared by using quantitative RT-PCR to detect the levels of SPRR1A, SPRR1B, SPRR3, and SPRR4 transcripts: (B) Cells were cultured in vitro from human BCCs then treated with varying concentrations of gremlin 1 or BMP 4 protein for 7 days. Cells were counted by using a hemacytometer, with triplicate counts taken for each measurement; each measurement is the average of duplicate experiments.

A Functional Response to gremlin 1 in Cultured Human Skin Epithelial Cells. We reasoned that if the functional role of gremlin 1 in maintaining a tumor cell niche was analogous to its role in the normal skin progenitor cell niche, gremlin 1 might be capable of inhibiting differentiation and promoting expansion of keratinocytes. To directly examine the effects of gremlin 1 on BCC tumor cells, cells isolated from fresh BCC tumors were cultured in the presence of recombinant human BMP 4, recombinant mouse gremlin 1, or both, and allowed to expand for 7 days. The resulting cell populations were compared by using quantitative RT-PCR to characterize their differentiation state (FIG. 3A). Compared with untreated controls, cells maintained in BMP 4 exhibited elevated mRNA levels of SPRR1A, SPRR1B, SPRR3, and SPRR4, established markers of differentiated keratinocytes. Gremlin 1 strongly attenuated this effect. Gremlin 1 protein alone, in the absence of exogenously added BMP 4, had little effect on SPRR expression. It may be noted that basal media contains no detectable BMP.

Gremlin 1 also antagonized BMP-mediated repression of cell proliferation. Primary BCC keratinocytes were cultured and cell growth assessed in the presence of varying concentrations of recombinant human BMP 4 and recombinant mouse gremlin 1 (FIG. 3B). The doubling time of these cells in culture with no added BMP or gremlin 1 was 3.1 (±0.1) days. Addition of gremlin 1 in the absence of added BMP 4 did not significantly affect growth rate, even at the highest concentration of gremlin (2.105 µg/ml). In the absence of gremlin 1, doubling time increased steadily with increasing BMP 4 concentration, reaching a maximum of 7.4 (±0.1) days, 2.4 times the baseline doubling rate. At the highest level of BMP 4, increasing the concentration of gremlin 1 protein steadily lowered the doubling time back to baseline. These results indicated that BMP 4 inhibits the expansion of BCC cell populations in culture, and that gremlin 1 attenuates this inhibition.

Figure 4:
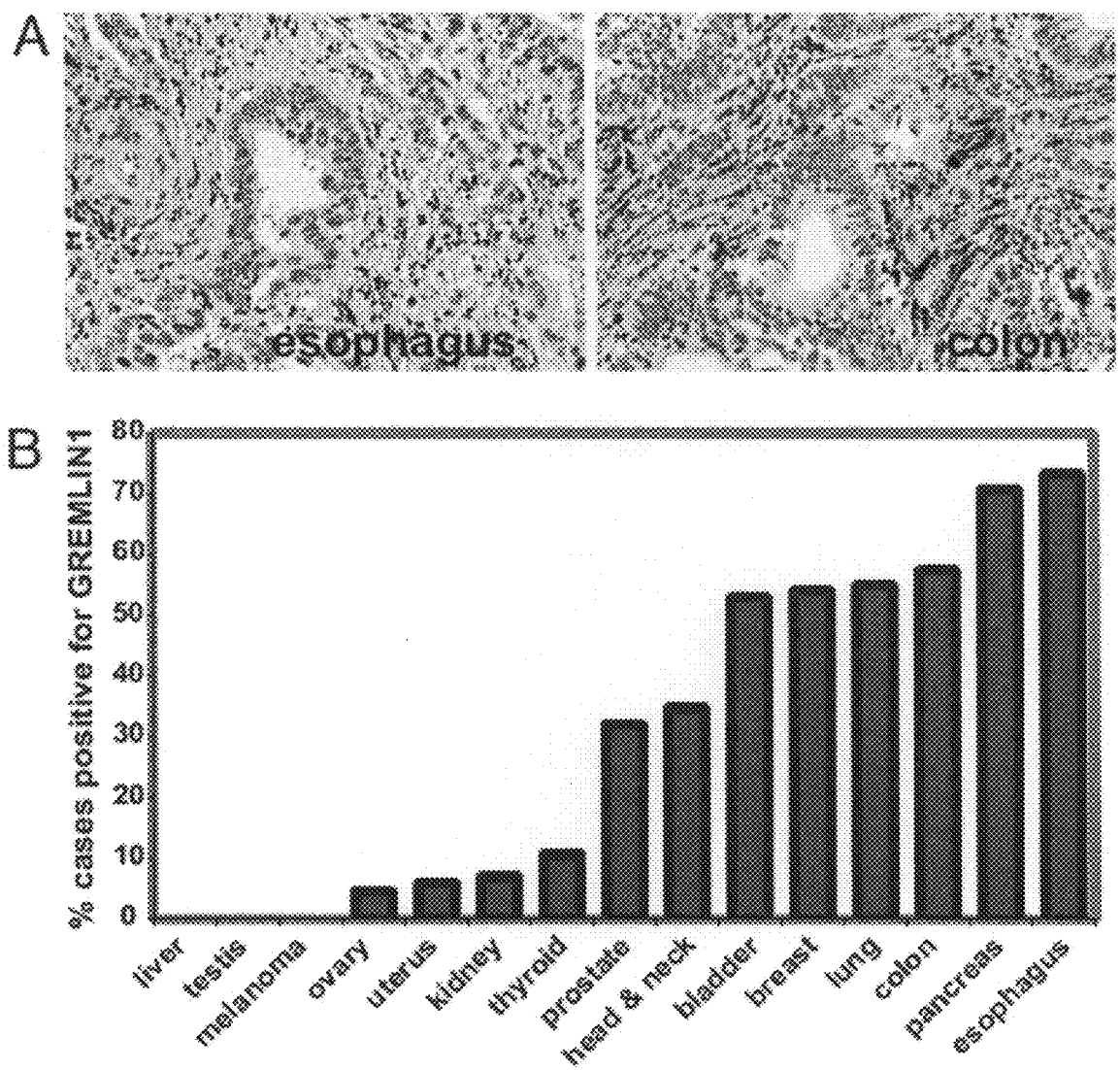
FIG. 4. GREMLIN 1 RNA is widely expressed in cancer. (A) Representative images for ISH in other carcinomas. Tissue microarrays representing 774 human cancers of diverse tissue types were analyzed for expression of GREMLIN 1 RNA. Positive signal is denoted by dark brown staining. (B) Tabulation of results for all tumor types examined for which n was >10.
Figure 7:
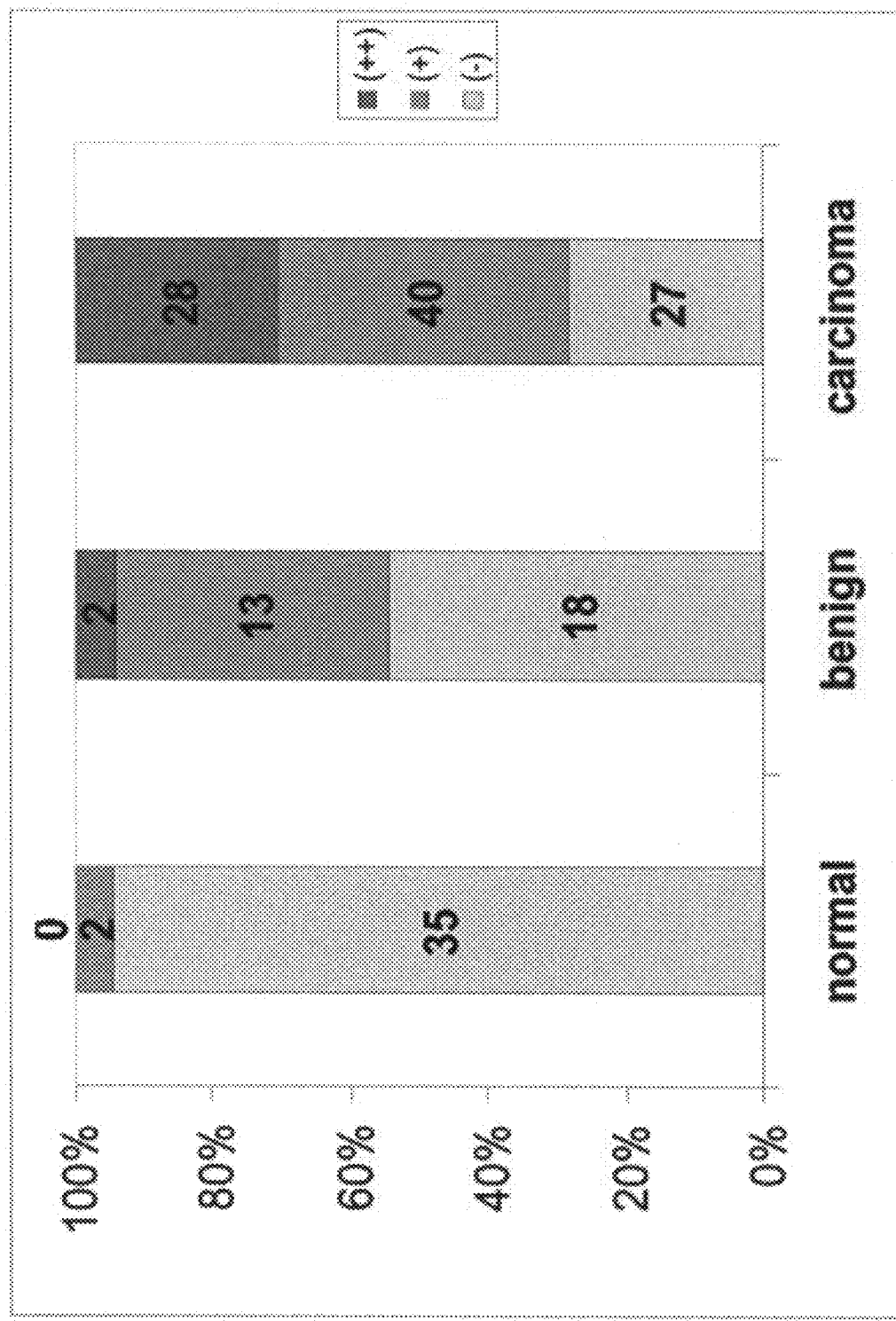
FIG. 7. GREMLIN 1 RNA expression in human pancreatic tissue. ISH was performed on tissue microarrays of paraffin-embedded samples of pancreatic tissue, including normal pancreas, benign pancreatic disease, and pancreatic carcinoma. Expression was scored as negative, low, or high and then tabulated for each class of pancreatic sample.

GREMLIN 1 Is Expressed by Stromal Cells in Diverse Human Carcinomas. GREMLIN 1 is highly expressed in the fibroblasts of most BCCs and undetectable in most normal skin sites. Evidence that BMPs regulate stem cell expansion in many tissues (skin, intestine, and blood) indicates that expression of gremlin 1 may be an important feature of the tumor microenvironment in other cancers. We therefore examined GREMLIN 1 RNA expression in a total of 774 tumors, including melanoma and carcinomas of the liver, testis, ovary, uterus, kidney, thyroid, prostate, head and neck, bladder, breast, lung, colon, pancreas, and esophagus (n>11-260 samples of each) by ISH to tissue microarrays. GREMLIN 1 was expressed by stromal cells in at least 50% of samples in carcinoma of the bladder, breast, lung, colon, pancreas, and esophagus, and in at least 25% of prostate and head and neck cancers (FIG. 4). Expression of GREMLIN 1 was exclusively localized to the stromal cells, with the exception of some breast and prostate samples, which showed limited expression in the tumor cells themselves. We also examined large sections of breast, pancreas, lung, and intestine, both tumor and nontumor. GREMLIN 1 expression was undetectable in normal and benign breast tissue. In a series of 165 samples of pancreas, including normal tissue and benign and malignant lesions, we detected GREMLIN 1 RNA in only 5% (2/37) of normal samples, compared with 71.5% of pancreatic tumors (68/95) (FIG. 7). GREMLIN 1 expression was also detected in 45% (15/33) of benign pancreatic disease samples, including pancreatitis, benign neuroendocrine tumors, and benign adenomas. In normal lung tissue, we observed GREMLIN 1 RNA in only a few smooth muscle cells. In large sections of both adenocarcinoma of the lung and adjacent normal lung tissue, there was no detectable GREMLIN 1 mRNA in the normal lung, whereas the tumor stroma and not the tumor cells themselves showed expression of GREMLIN 1 mRNA (FIG. 8). In normal intestine, no GREMLIN 1 expression was observed except in the lamina propria, in what appear by morphology to be smooth muscle cells.

We found that the BMP antagonist GREMLIN 1 is frequently expressed by stromal cells in the microenvironment of human carcinomas, including BCC, and can enhance cell expansion and block differentiation in vitro. Carcinomas are histologically complex tissues comprising not only tumor cells but also fibroblasts, smooth muscle cells, endothelial cells, adipocytes, and leukocytes, as well as components of the extracellular matrix. Interactions with these cells and factors in the tumor microenvironment, or tumor cell niche, may also play a critical role in the initiation and progression of cancer. We used a genomic approach to identify factors differentially expressed by BCC-associated fibroblasts compared with their non-tumor associated counterparts.

Figure 5:
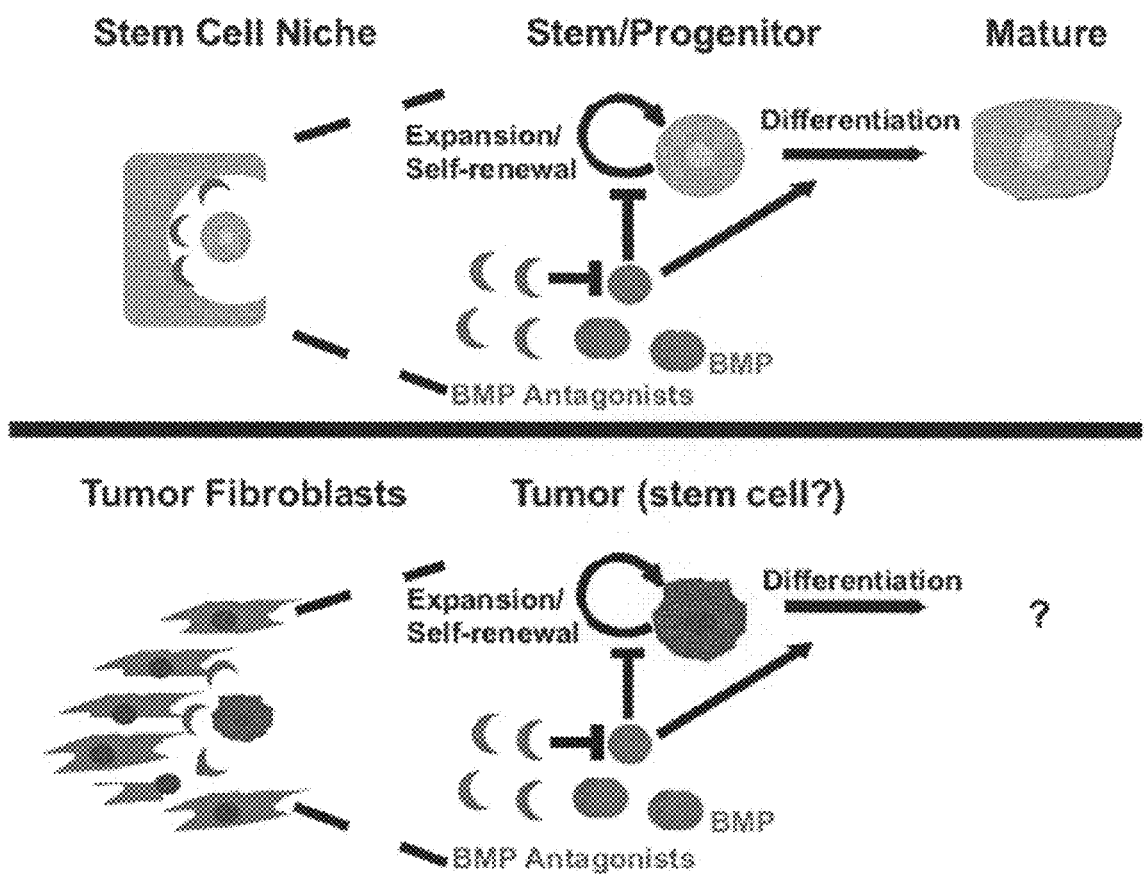
FIG. 5. A possible parallel for the role of BMPs and BMP antagonists in the tumor stem cell niche and normal stem cell niche. BMPs can induce differentiation and block expansion of normal stem and progenitor cells. (Upper) BMP antagonists can reverse this effect and favor expansion. Signals that are critical for stem cell self renewal, such as BMP antagonists, derive from the stem cell niche. BMPs may often come from epithelial or stem cells. (Lower) In tumor biology, BMPs can also inhibit expansion of tumor cells. BMP antagonists secreted by the tumor cell niche may reverse this inhibition, allowing tumor cell expansion to continue.

Global gene expression profiling of these two cell populations revealed intrinsic, systematic differences in gene expression programs. We chose to focus on one gene in particular, the BMP antagonist GREMLIN 1. In many settings, BMPs promote differentiation of stem cells, thus promoting exit from the stem cell compartment. These observations led us to hypothesize that BMP antagonists may define a niche for a self-renewing population in some cancers. In this model, the role of BMPs and their antagonists in regulating a self-renewing tumor cell compartment parallels their role in regulating the normal stem cell compartment (FIG. 5). In normal physiology, factors (including the BMP antagonists) that support "stemness" of stem cells are often provided by a stem cell "niche," a molecular microenvironment defined by a localized population of cells that regulates the size of the stem cell compartment. Our data demonstrate a directly analogous model for the tumor context in which the tumor cells require BMP antagonists coming from the tumor fibroblasts (another specialized stromal compartment) to maintain their expansion.

Our results represent a dramatic example of the differences between stromal cells in cancer and those in the normal tissue counterpart. Elevated expression of GREMLIN 1 has previously been documented in a small subset of cells in normal skin, the putative epithelial stem cells, compared with other normal skin epithelial cells. In our study, GREMLIN 1 RNA was expressed in stromal cells of nearly all BCC samples examined, but undetectable in the vast majority of normal skin sites. The cells that express GREMLIN 1 have the appearance and immunohistochemical characteristics of fibroblasts and not cells of epithelial, lymphocytic, endothelial, smooth muscle, or glial origin.

Figure 9:
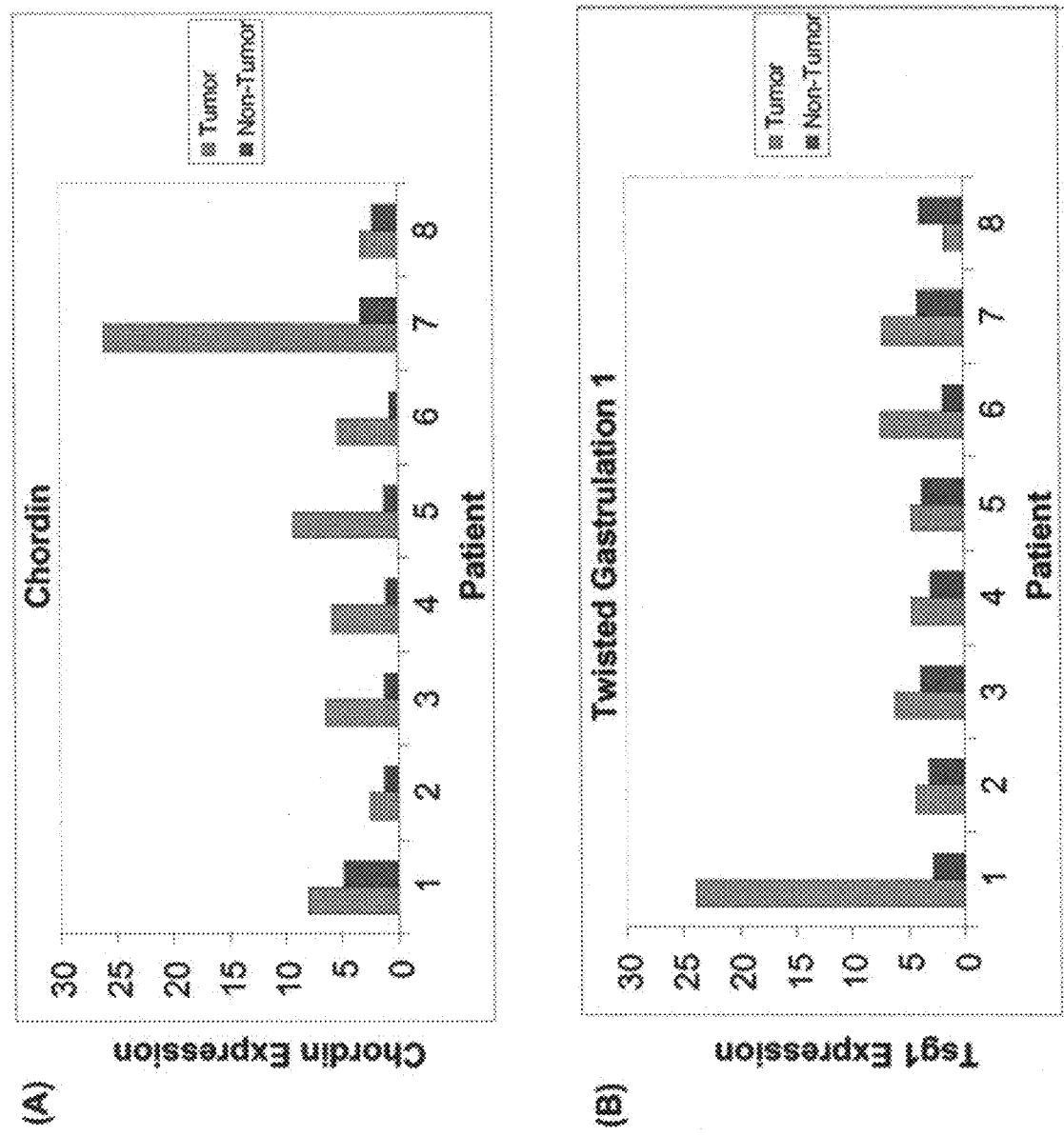
FIG. 9. Expression of other bone morphogenetic protein (BMP) antagonists in BCC tumor and nontumor tissue. RT-PCR analysis of expression of BMP antagonists CHORDIN and TSG1. Transcript levels in whole tumor skin were compared to those in adjacent nontumor whole tissue from the same patient. The expression level for each gene in a sample has been normalized to averaged duplicate measurements of GAPDH for that sample.

We have used RT-PCR to examine the expression of a number of other reported BMP antagonists, including TSG1, FOLLISTATIN, NOGGIN, and CHORDIN, in whole tissue samples of human BCC and matched nontumor tissue. Like GREMLIN 1, both TSG1 and CHORDIN were typically expressed at higher levels in tumors compared with nontumor controls (FIG. 9). Along with GREMLIN 1, other genes that were elevated in BCC tumor associated fibroblasts included a number of components of the Wnt signaling pathway, such as DICKKOPF HOMOLOG 1 (DKK1), a secreted protein inhibitor of the Wnt signaling pathway. The Wnt proteins (along with BMPs) are targets of the Sonic Hedgehog pathway.

We have shown that BMP inhibits expansion of BCC cells in culture, and that gremlin 1 can overcome this inhibition. The data on cultured cells from BCC tumors suggest that the effects of gremlin are mediated exclusively through the BMP pathway, because gremlin 1 had no appreciable effect on cell expansion unless BMP was present. The tumor cells in vitro showed a response to gremlin 1 only in the presence of exogenous BMP.

The expression of GREMLIN 1 by stromal cells in diverse human carcinomas, in contrast to its rare expression in corresponding normal tissues, suggests that expression by cells in the tumor microenvironment of factors that regulate the self renewal of the tumor cells may be a general feature of human cancer. Inhibiting these critical molecular signals from the tumor microenvironment provides a useful therapeutic strategy.

Materials and Methods

Primary Human Cells. Stromal cells were isolated from discarded skin tissue from the Dermatology. Clinic with approval from the Institutional Review Board (Stanford University Medical Center). Fat was removed by using a sterile scalpel and forceps; tissue was minced into ~1-mm cubes. Incubation in a six-well dish without medium at 37° C. for 10 min allowed for adhesion of the tissue to the plate. Fresh media containing DMEM, 10% FBS, and penicillin-streptomycin were added, and samples were maintained at 37° C. and 5% $CO_2$. Media were replaced every 2 days. Outgrowth of spindle-shaped cells was typically apparent after 5-15 days in culture and had a success rate of ~60%. When the cells were near confluence, they were subcultured with 0.25% trypsin-EDTA. Cultures were expanded until sufficient for RNA isolations (typically four passages).

Human BCC keratinocyte cultures were derived from fresh skin tissue as described. A small cross-sectional piece of each sample was cut and fixed in 10% buffered formalin for histological confirmation. The remaining tissue was placed overnight in 5 mg/ml dispase (Gibco, Carlsbad, Calif.) at 4° C. The next day, epidermis was separated from dermis with dissecting forceps, minced by using sterile forceps and scalpel, and incubated in 0.05% trypsin-EDTA at 37° C. for 15 min, with occasional mixing to disperse cells. After neutralization with HBSS containing 15% FBS, cells were spun down at 900 rpm in a Beckman Allegra GR centrifuge for 5 min, then resuspended in Keratinocyte serum-free media supplemented with EGF, bovine pituitary extract, and penicillin-streptomycin (Gibco). Cells were plated onto 12-well collagen I-coated plates (BD Biosciences, Franklin Lakes, N.J.) and incubated at 37° C. in 5% $CO_2$. Media were replaced every 2 days. Contamination from fibroblasts or normal keratinocytes was avoided by subjecting the culture to differential trypsinization and a transient increase in calcium concentration, respectively.

Microarray Procedures. Construction of human cDNA microarrays with ~42,000 elements, representing >24,000 genes, and hybridizations was as described. Forty-eight hours before RNA harvest of stromal cultures, cells were washed three times in pre-warmed PBS and then maintained in low serum media containing DMEM and 0.1% FBS. mRNA was harvested by using the FastTrack kit (invitrogen, Carlsbad, Calif.). Universal Human Reference RNA (Stratagene, La Jolla, Calif.) was used as reference for array experiments. Arrays were scanned with a GenePix 4000A scanner and images analyzed with GenePix 3.0 (Axon Instruments, Union City, Calif.). Microarray data were stored in the Stanford Microarray Database. All microarray data are publicly available. We considered only genes for which the cognate array element had a fluorescent signal at least 1.5-fold greater than the local background signal in both channels.

Significance Analysis of Microarrays was then used to identify a set of genes whose expression levels were significantly different between five tumor- and five non-tumor-derived stromal cell cultures at a false discovery rate of 15% or 5%. Resulting expression patterns were organized by hierarchical clustering.

ISH. Digoxigenin-labeled sense and antisense riboprobes for GREMLIN 1 were synthesized by using T7 polymerase-directed in vitro transcription of linearized plasmid DNA (IMAGE clone 7262108) by using the DIG RNA Labeling Kit (Roche Diagnostics). ISH on paraffin sections was performed by using a biotinyl tyramide amplification procedure, essentially as previously described. Results were considered specific when a strong pattern of distinct punctate staining was seen for the antisense probe, and little or no staining was observed for the corresponding sense probe. Tissue microarrays of tumor samples were made as described.

IHC. IHC staining for Gremlin 1 was performed with Dako Envision Plus (Glostrup, Denmark). Anti-gremlin 1 antibody (Imgenex, San Diego, Calif.) was used at 1:10 dilution. IHC for BMPs was performed by using Vectastain ELITE ABC Rabbit IgG (Vector Laboratories, Burlingame, Calif.). Anti-BMP 2 and 4 antibodies (Santa Cruz Biotechnology, Santa Cruz, Calif.) were used at 1:50 dilution. IHC for cell lineage specific markers was performed by using the Vectastain ELITE ABC Mouse IgG kit with antibodies against Vimentin (1:200), CD31 (1:30), CD45 (1:100), GFAP (1:100), Desmin (1:100), and pancytokeratin (1:100; Dako). In all cases, antigen retrieval consisted of a microwave step in 10 mM citrate buffer. Nuclei were stained with hematoxylin. As positive and negative controls, each antibody was also tested on a tissue microarray containing a large variety of normal and tumor human tissue samples to confirm the nominal specificity. ISH and IHC images were acquired with the BLISS Microscope System (Bacus Laboratories, Lombard, Ill.).

In Vitro Expansion and Differentiation Assays. To assess the effects of gremlin 1 and BMP proteins on expansion of cells in vitro, BCC-derived cells were maintained in keratinocyte growth media containing bovine pituitary extract, human EGF, bovine insulin, hydrocortisone, gentamicin, and amphotericin B (Clonetics, San Diego, Calif.). Cells were incubated with recombinant mouse gremlin 1 and/or recombinant human BMP 2 or 4 (R&D Systems, Minneapolis, Minn.) at the concentrations indicated. Cell number was assessed by using triplicate counts with a hemacytometer, or RNA was collected for RT-PCR analysis.

Quantitative RT-PCR. Total RNA was isolated from whole tissue, either tumor or adjacent non-tumor tissue from the same patient, by using the RNeasy Fibrous Tissue Mini kit (Qiagen, Chatsworth, Calif.) and a rotor homogenizer. Total RNA was isolated from cultured cells by using RNeasy Mini (Qiagen). First-strand. DNA was generated from mRNA by using the SuperScript III First-Strand Synthesis System (Invitrogen). RT-PCR (TaqMan) was performed by using ABI 7300 (Applied Biosystems, Foster City, Calif.) with duplicate experimental samples for each sample and each probe/primer set. GAPDH was used for normalizing PCR results.

These results are published in Sneddon et al. (2006) PNAS 103:14842, herein specifically incorporated by reference.

What is claimed is:

1. A method for the detection of a tumor-associated stromal cell, the method comprising:
   detecting the level of expression of Gremlin 1 mRNA or protein in candidate tumor-associated stromal cells;
   comparing the level of expression of Gremlin 1 mRNA or protein in said candidate tumor-associated stromal cells to normal stromal cells, wherein increased levels of expression of Gremlin 1 in said candidate tumor-associated stromal cells is indicative that said cells are tumor-associated stromal cells.

2. The method according to claim 1, wherein increased amounts of Gremlin 1 mRNA are detected in said candidate tumor associated stromal cells.

3. The method of claim 1, wherein the tumor is a carcinoma.

4. The method of claim 1, wherein said increased amounts of Gremlin 1 polypeptide are detected in said candidate tumor associated stromal cells.

* * * * *